United States Patent [19]
Ansmann

[11] Patent Number: 6,033,652
[45] Date of Patent: Mar. 7, 2000

[54] HAIR-TREATMENT FORMULATIONS

[75] Inventor: Achim Ansmann, Erkrath, Germany

[73] Assignee: Henkel Kommanditgesellschaft auf Aktien, Duesseldorf, Germany

[21] Appl. No.: 08/857,442

[22] Filed: May 15, 1997

Related U.S. Application Data

[60] Provisional application No. 60/024,652, Aug. 22, 1996.

[30] Foreign Application Priority Data

May 15, 1996 [DE] Germany .......................... 196 19 645

[51] Int. Cl.$^7$ ................. A61K 7/06; A61K 7/48
[52] U.S. Cl. .................... 424/70.122; 424/70.1; 424/70.12
[58] Field of Search ............... 424/70.1, 70.12, 424/70.122

[56] References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,703,798 | 3/1955 | Schwartz | 260/211 |
| 4,172,887 | 10/1979 | Vanlerberghe et al. | 424/70 |
| 4,559,227 | 12/1985 | Chandra et al. | 424/70 |
| 4,591,610 | 5/1986 | Grollier | 524/55 |
| 4,704,272 | 11/1987 | Oh et al. | 424/70 |
| 4,728,457 | 3/1988 | Fieler et al. | 252/174.15 |
| 4,741,855 | 5/1988 | Grote et al. | 252/142 |
| 5,009,814 | 4/1991 | Kelkenberg et al. | 252/548 |
| 5,374,716 | 12/1994 | Biermann et al. | 536/18.6 |
| 5,403,508 | 4/1995 | Reng et al. | 252/174.22 |
| 5,576,425 | 11/1996 | Hill et al. | 536/18.6 |
| 5,700,456 | 12/1997 | Dubief | 424/70.17 |

FOREIGN PATENT DOCUMENTS

| | | |
|---|---|---|
| 2 006 248 | 6/1990 | Canada . |
| 0 285 768 | 10/1988 | European Pat. Off. . |
| 0 301 298 | 2/1989 | European Pat. Off. . |
| 0337354 A1 | 10/1989 | European Pat. Off. . |
| 0 376 083 | 7/1990 | European Pat. Off. . |
| 0 557 399 | 9/1993 | European Pat. Off. . |
| 0 570 398 | 11/1993 | European Pat. Off. . |
| 0337354 B1 | 2/1994 | European Pat. Off. . |
| 0 398 177 | 8/1995 | European Pat. Off. . |
| 1 580 491 | 9/1969 | France . |
| 2 252 840 | 8/1975 | France . |
| 25 42 997 | 9/1984 | France . |
| 11 65 574 | 3/1964 | Germany . |
| 20 24 051 | 5/1986 | Germany . |
| 43 09 567 | 9/1994 | Germany . |
| 44 00 632 | 3/1995 | Germany . |
| 4403258 | 3/1995 | Germany . |
| 4326958 | 7/1995 | Germany . |
| 962 919 | 7/1964 | United Kingdom . |
| 1 333 475 | 10/1973 | United Kingdom . |
| WO 90/03977 | 4/1990 | WIPO . |
| WO 92/06984 | 4/1992 | WIPO . |
| WO 92/13512 | 8/1992 | WIPO . |
| WO 95/13863 | 5/1995 | WIPO . |

OTHER PUBLICATIONS

Ansmann, et al., "Perlglanz in modernen, tensidhaltigen Formulierungen", Parf. Kosm. 75, (1994) pp. 578–580.
H. Kelkenberg, "Detergenzien auf Zuckerbasis", Tens. Surf. Det. 25 (1988) pp. 8–13.
Dr. K. Schnurrbusch, Seifen–Öle–Fette–Wachse, 100, Apr. 4, 1974, pp. 173–177.
"Kosmetische Färbemittel", Farbstoffkommission der Deutschen Forschungsgemeinschaft, Verlag Chemie, Weinheim, 1984, pp. 81–106.

*Primary Examiner*—Thurman K. Page
*Assistant Examiner*—Brian K. Seidleck
*Attorney, Agent, or Firm*—Ernest Szoke; Wayne C. Jaeschke; Glenn E.J. Murphy

[57] ABSTRACT

The invention relates to new hair-treatment formulations containing
(a) 1 to 30% by weight of sugar surfactants,
(b) 1 to 10% by weight of silicone compounds liquid at room temperature and
(c) less than 2% by weight of pearlescing waxes, with the proviso that the formulations are made up to 100% by weight with water and typical additives. The formulations are stable against clouding and show improved brilliant pearlescence.

1 Claim, No Drawings

HAIR-TREATMENT FORMULATIONS

BENEFIT UNDER 37 C.F.R. 1.78 (A)(4)

This application claims benefit of earlier filed and copending U.S. Provisional Application Ser. No. 60/024,652, filed Aug. 22, 1996, the entire disclosure of which hereby is incorporated by reference.

BACKGROUND OF THE INVENTION

1. Field of the Invention

This invention relates to hair-treatment formulations with a certain content of sugar surfactants, selected silicone compounds and pearlescing waxes.

2. Description of the Related Art

Since the beginning of the sixties, silicone compounds have acquired increasing significance as constituents of cosmetic preparations because they improve the feeling the preparations leave on the hair and skin, even in small quantities, are chemically inert, are compatible with virtually all cosmetic ingredients and, finally, are dermatologically safe. Sugar surfactants of the alkyl glucoside or fatty acid-N-alkyl glucamide type show excellent performance properties coupled with particular skin-cosmetic compatibility and, accordingly, are also preferred surfactants for the production of, for example, hair shampoos and manual dishwashing detergents to which substances imparting pearlescence to the formulations through the scattering of light at minute crystals are often added for aesthetic reasons. A review of modern pearlescing formulations was published by A. Ansmann et al. in Parf. Kosm. 75, 578 (1994).

Pearlescing concentrates containing acylated ethylene glycols together with alkyl glucosides are known, for example, from European patents EP-B1 0 376 083 and EP-B1 0 570 398 (Henkel) and from International patent application WO 95/13863 (SEPPIC).

Compositions containing alkyl oligoglycosides, silicones liquid at room temperature and pearlescing waxes are described in European patents EP-B1 0 337 354 and EP-B1 0 398 177 (Kao). Thus, in Examples 2 and 3 for example, EP-B1 0 398 177 discloses shampoo compositions containing 20% by weight of alkyl glucoside, 3% by weight of liquid siloxanes and 2% by weight of pearlescing waxes, namely ethylene glycol distearate. It has been found in practice that formulations of this type are not stable, become inhomogeneous and thicken up. Although their opacity is concealed by the presence of pearlescing waxes, the preparations are not sparkling in their appearance, but dull-looking which is often equated by the consumer with such terms as "spoiled" or "out-of-date". It is clear that any such product will attract little consumer interest despite its satisfactory properties.

European patent EP-B1 0 557 399 (L'Oreal) describes similar preparations which, in addition to alkyl glucosides and pearlescing waxes, also contain silicones. However, the silicones in question are not resin-like substances solid at room temperature which would be of at most only limited use, for example for the production of hair shampoos, because they could easily lead to sticking of the hair strands. Finally, cosmetic preparations containing short-chain alkyl glucosides and hydroxy modified polysiloxanes are known from French patent FR-B 25 42 997 (L'Oreal). However, these preparations do not contain any pearlescing waxes. In addition, pearlescent shampoos containing silicones are disclosed in U.S. Pat. No. 4,559,227 (Dow) and in U.S. Pat. No. 4,704,272 and U.S. Pat. No. 4,741,855 (Procter & Gamble).

Accordingly, the problem addressed by the present invention was to provide pearlescent hair treatment formulations based on the sugar surfactants mentioned and liquid silicone compounds which would be sufficiently stable in storage and which would show a brilliant, finely crystalline pearlescence.

DESCRIPTION OF THE INVENTION

The present invention relates to hair treatment formulations containing (a) 1 to 30% by weight of sugar surfactants,
(b) 1 to 10% by weight of silicone compounds liquid at room temperature and
(c) less than 2% by weight of pearlescing waxes, with the proviso that the formulations are made up to 100% by weight with water and typical additives.

In the course of extensive studies, applicants have found that, surprisingly, inhomogeneities can be reliably avoided in known hair shampoos if the content of pearlescing waxes in the shampoos is adjusted to less than 2% by weight, preferably to between 0.1 and 1.5% by weight and more preferably to between 0.5 and 1.0% by weight. The resulting preparations are stable in storage, even under varying temperature conditions, i.e. no clouding occurs, viscosity remains constant and their pearlescence has the required brilliance and crystal fineness.

Alkyl and/or Akenyl Oligoglycosides

Alkyl and alkenyl oligoglycosides are known nonionic surfactants which correspond to formula (I):

$$R^1O-[G]_p \qquad (I)$$

where $R^1$ is an alkyl and/or alkenyl radical containing 4 to 22 carbon atoms, G is a sugar unit containing 5 or 6 carbon atoms and p is a number of 1 to 10.

They may be obtained by the relevant methods of preparative organic chemistry. EP-A1-0 301 298 and WO 90/03977 are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1. 1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred, being used in quantities of 1 to 30% by weight and preferably 5 to 20% by weight, based on the formulation.

Fatty Acid N-Alkyl Polyhydroxyalkylamides

Fatty acid N-alkyl polyhydroxyalkylamides are nonionic surfactants which correspond to formula (II):

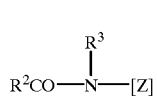

(II)

where $R^2CO$ is an aliphatic acyl radical containing 6 to 22 carbon atoms, $R^3$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups. The fatty acid N-alkyl polyhydroxyalkylamides are known compounds which may normally be obtained by reductive amination of a reducing sugar with ammonia, an alkylamine or an alkanolamine and subsequent acylation with a fatty acid, a fatty acid alkyl ester or a fatty acid chloride. Processes for their production are described in U.S. Pat. No. 1,985,424, in U.S. Pat. No. 2,016,962 and in U.S. Pat. No. 2,703,798 and in International patent application WO 92/06984. An overview of this subject by H. Kelkenberg can be found in Tens. Surf. Det. 25, 8 (1988).

The fatty acid N-alkyl polyhydroxyalkylamides are preferably derived from reducing sugars containing 5 or 6 carbon atoms, more particularly from glucose. Accordingly, the preferred fatty acid N-alkyl polyhydroxyalkylamides are fatty acid N-alkyl glucamides which correspond to formula (III):

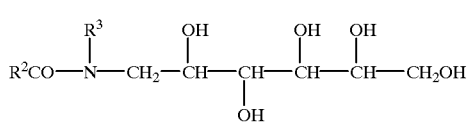

(III)

Preferred fatty acid N-alkyl polyhydroxyalkylamides are glucamides corresponding to formula (III) in which $R^3$ is an alkyl group and $R^2CO$ represents the acyl component of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof. Fatty acid N-alkyl glucamides (III) obtained by reductive amination of glucose with methylamine and subsequent acylation with lauric acid or $C_{12/14}$ coconut oil fatty acid or a corresponding derivative are particularly preferred. In addition, the polyhydroxyalkylamides may also be derived from maltose and palatinose. The amides are preferably used in quantities of 1 to 30% by weight and, more particularly, in quantities of 5 to 25% by weight. Mixtures with the above-mentioned alkyl and/or alkenyl oligoglycosides in a ratio by weight of 10:90 to 90:10, preferably 25:75 to 75:25 and more preferably 40:60 to 60:40 may also be used.

The use of fatty acid N-alkyl polyhydroxyalkylamides is also the subject of a number of publications. For example, their use as thickeners is known from European patent application EP-A1 0 285 768 (Hüls). FR-A 1 580 491 (Henkel) describes water-containing detergent mixtures based on sulfates and/or sulfonates, nonionic surfactants and optionally soaps which contain fatty acid N-alkyl glucamides as foam regulators. Mixtures of short-chain and relatively long-chain glucamides are described in DE-C1 44 00 632 (Henkel). In addition, DE-C2 42 36 958 and DE-A1 43 09 567 (Henkel) report on the use -of glucamides with relatively long alkyl chains as pseudoceramides in skin-care formulations and on combinations of glucamides with protein hydrolyzates and cationic surfactants in hair-care products.

Liquid Silicone Compounds

The silicone compounds used as component (b) in accordance with the invention are liquid at room temperature, i.e. at temperatures in the range from 18 to 25° C., and are preferably dimethyl polysiloxanes or methylphenyl polysiloxanes. A review of such silicone compounds was published, for example, by K. Schnurrbusch in Seifen-Fette-Öle-Wachse 100, 173 (1974). Other suitable substances are amino modified silicones, for example of the Amodimethicone type, and open-chain or cyclic silicone compounds optionally substituted by fatty acid, alcohol, polyether, epoxy, fluorine or alkyl groups. A review of the substances in question can be found in EP-B1 0 398 177 of which the teaching on the nature of the silicone compounds is hereby expressly included. The silicones may be used in quantities of 1 to 10% by weight and are preferably used in quantities of 2 to 5% by weight, based on the formulation.

Pearlescing Waxes

Preferred pearlescing waxes are acylation products of glycols and self-condensation products thereof which correspond to formula (IV):

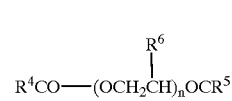

(IV)

in which $R^4CO$ and $R^5CO$ independently of one another represent saturated or unsaturated acyl radicals containing 8 to 22 and preferably 12 to 18 carbon atoms, $R^6$ is hydrogen or a methyl group and n is a number of 1 to 5. Acylation products of ethylene glycol with cocofatty acid or stearic acid, more particularly ethylene glycol distearate, are preferred for this purpose.

Another group of pearlescing waxes are fatty acid partial esters corresponding to formula (V):

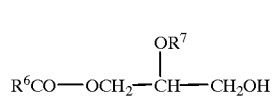

(V)

in which $R^6CO$ is a saturated or unsaturated acyl radical containing 6 to 22 and preferably 12 to 18 carbon atoms and $R^7$ is hydrogen or an acyl radical $R^6CO$. Typical examples are mono- and diglycerides and technical mixtures thereof which may still contain small amounts of trifatty acid esters from their production. They have the advantage over acylated glycols that they do not contain any ethylene oxide units which is preferred by various manufacturers of cosmetic preparations. Accordingly, one preferred embodiment of the invention is characterized for example by the use of mono/diglyceride mixtures derived from lauric acid, coconut oil fatty acid, palmitic acid, oleic acid and, more particularly, stearic acid.

In addition to the conventional pearlescing waxes mentioned above, inorganic pearlescing pigments, for example of the coated montmorillonite type, may also be used.

Commercial Applications

The hair treatment formulations according to the invention may contain surfactants compatible with the other ingredients. Typical examples are fatty alcohol polyglycol ether sulfates, monoglyceride sulfates, mono- and/or dialkyl sulfosuccinates, fatty acid isethionates, fatty acid sarcosinates, fatty acid taurides, ether carboxylic acids, alkyl amidobetaines and/or, preferably, vegetable protein fatty acid hydrolyzates or condensates thereof with fatty acids. In addition, they may contain oils, emulsifiers, superfatting agents, stabilizers, waxes, consistency regulators, thickeners, cationic polymers, biogenic agents, film formers, preservatives, hydrotropes, UV absorbers, dyes and fragrances as further auxiliaries and additives.

Suitable oils are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer diol) and/or Guerbet alcohols, triglycerides based on $C_{6-10}$ fatty acids, vegetable oils, branched primary alcohols, substituted cyclohexanes, Guerbet carbonates, dialkyl ethers and/or aliphatic or naphthenic hydrocarbons.

Nonionic, ampholytic and/or zwitterionic surface-active compounds distinguished by a lipophilic, preferably linear, alkyl or alkenyl group and at least one hydrophilic group may be used as emulsifiers or co-emulsifiers. The hydrophilic group may be both an ionic group and a nonionic group. Nonionic emulsifiers contain, for example, a polyol group, a polyalkylene glycol ether group or a combination of a polyol and a polyglycol ether group as the hydrophilic group.

Preferred formulations are those containing nonionic surfactants from at least one of the following groups as o/w emulsifiers:

(a1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group;

(a2) $C_{12/18}$ fatty acid monoesters and diesters of adducts of 1 to 30 moles of ethylene oxide with glycerol;

(a3) glycerol monoesters and diesters and sorbitan monoesters and diesters of saturated and unsaturated fatty acids containing 6 to 22 carbon atoms and ethylene oxide adducts thereof;

(a4) adducts of 15 to 60 moles of ethylene oxide with castor oil and/or hydrogenated castor oil;

(a5) polyol esters and, in particular, polyglycerol esters such as, for example, polyglycerol polyricinoleate or polyglycerol poly-12-hydroxystearate.

Mixtures of compounds from several of these classes are also suitable.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Suitable w/o emulsifiers are:

(b1) adducts of 2 to 15 moles of ethylene oxide with castor oil and/or hydrogenated castor oil;

(b2) partial esters based on linear, branched, unsaturated or saturated $C_{12/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose);

(b3) trialkyl phosphates;

(b4) wool wax alcohols;

(b5) polysiloxane/polyalkyl polyether copolymers and corresponding derivatives;

(b6) mixed esters of pentaerythritol, fatty acids, citric acid and fatty alcohol according to DE-PS 11 65 574 and (b7) polyalkylene glycols.

Superfatting agents may be selected from such substances as, for example, polyethoxylated lanolin derivatives, lecithin derivatives, polyol fatty acid esters, monoglycerides and fatty acid alkanolamides, the fatty acid alkanolamides also serving as foam stabilizers. Suitable consistency regulators are, above all, fatty alcohols containing 12 to 22 and preferably 16 to 18 carbon atoms. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more particularly xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone, surfactants such as, for example, narrow-range fatty alcohol ethoxylates or alkyl oligoglucosides and electrolytes, such as sodium chloride and ammonium chloride.

Suitable cationic polymers are, for example, cationic cellulose derivatives, cationic starch, copolymers of diallyl ammonium salts and acrylamides, quaternized vinyl pyrrolidone/vinyl imidazole polymers such as, for example, LUVIQUAT® (BASF AG, Ludwigshafen, FRG), condensation products of polyglycols and amines, quaternized collagen polypeptides such as, for example, Lauryldimonium Hydroxypropyl Hydrolyzed Collagen (LAMEQUAT® L, Grünau GmbH), quaternized wheat polypeptides, polyethyleneimine, cationic silicone polymers such as, for example, Amidomethicone or Dow Corning 929, Dow Corning Co., USA, copolymers of adipic acid and dimethylaminohydroxypropyl diethylenetriamine (CARTARETINE®, Sandoz AG, CH), polyaminopolyamides as described, for example, in FR-A 2 252 840 and crosslinked water-soluble polymers thereof, cationic chitin derivatives such as, for example, quaternized chitosan, optionally in microcrystalline distribution, cationic guar gum such as, for example, JAGUAR® CBS, JAGUAR® C-17, JAGUA® C-16 of Celanese, USA, quaternized ammonium salt polymers such as, for example, MIRAPOL® A-15, MIRAPOL® AD-1, MIRAPOL® AZ-1 of Miranol, USA.

Superfatting agents may be selected from such substances as, for example, polyethoxylated lanolin derivatives, lecithin derivatives, polyol fatty acid esters, monoglycerides and fatty acid alkanolamides, the fatty acid alkanolamides also serving as foam stabilizers. Typical examples of fats are glycerides while suitable waxes are inter alia beeswax, paraffin wax or microwaxes, optionally in combination with hydrophilic waxes, for example cetostearyl alcohol. Metal salts of fatty acids, for example magnesium, aluminium and/or zinc stearate, may be used as stabilizers. In the context of the invention, biogenic agents are, for example, panthenol, AHA acids, plant extracts and vitamin complexes. Suitable film formers are, for example, chitosan, microcrystalline chitosan, quaternized chitosan, polyvinyl pyrrolidine, vinyl pyrrolidone/vinyl acetate copolymers, polymers of the acrylic acid series, quaternary cellulose derivatives, collagen, hyaluronic acid or salts thereof and similar compounds. In addition, hydrotropes, for example ethanol, isopropyl alcohol, propylene glycol or glucose, may be used to improve flow behavior. Suitable preservatives are, for example, phenoxyethanol, formaldehyde solution, parabens, pentanediol or sorbic acid. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

The total percentage content of auxiliaries and additives may be 1 to 50% by weight and is preferably 5 to 40% by weight, based on the formulation. The formulations may be produced by standard cold or hot processes; they are preferably produced by the phase inversion temperature method.

EXAMPLES 1 to 2 g of pearlescing wax were melted and, after the addition of 15 g of sugar surfactant, 5 g of silicone compound and the other surface-active ingredients, the resulting melt was made up with water to 100 g. After homogenization, the shampoo formulations were stored for 1 week at 40° C. The viscosity of the products was determined by the Brookfield method (23° C., spindle, 10 r.p.m.) while the particle fineness of the pearlescent crystals was visually evaluated under a microscope on the scale of 1=very fine crystals to 5=coarse crystals. Pearlescence was also evaluated on a scale of 1=brilliant to 5=dull. Opacity was visually determined and evaluated as (+)=opaque or (−)=non-opaque. The results are set out in Table 1 (percentages as % by weight). Formulations F1 to F5 correspond to the invention while formulations F6 to F10 are intended for comparison.

TABLE 1

| Components | Pearlescent Shampoos | | | | | | | | | |
| --- | --- | --- | --- | --- | --- | --- | --- | --- | --- | --- |
| | F1 | F2 | F3 | F4 | F5 | F6 | F7 | F8 | F9 | F10 |
| Cocoalkyl oligoglucoside | 15.0 | 15.0 | 15.0 | 15.0 | – | 15.0 | 15.0 | 15.0 | 15.0 | – |
| Lauric acid-N-methyl glucamide | – | – | – | – | 15.0 | – | – | – | – | 15.0 |
| Cocoalcohol + 2EO sulfate Na salt | 10.0 | 10.0 | 10.0 | 10.0 | 10.0 | 10.0 | 10.0 | 10.0 | 10.0 | 10.0 |
| Dimethyl polysiloxane | 5.0 | 5.0 | – | – | 5.0 | 5.0 | 5.0 | – | – | 5.0 |
| Amodimethicone | – | – | 5.0 | 5.0 | – | – | – | 5.0 | 5.0 | – |
| Cocoamidopropyl Betaine | 5.0 | 5.0 | 5.0 | 5.0 | 5.0 | 5.0 | 5.0 | 5.0 | 5.0 | 5.0 |
| Esterquat* | 1.5 | 1.5 | 1.5 | 1.5 | 1.5 | 1.5 | 1.5 | 1.5 | 1.5 | 1.5 |
| Ethylene glycol distearate | 1.0 | – | 1.5 | – | – | 2.0 | – | 2.0 | – | – |
| Lauric acid monoglyceride | – | 0.5 | – | 1.5 | 1.0 | – | 2.0 | – | 2.0 | 2.0 |

TABLE 1-continued

| | Pearlescent Shampoos | | | | | | | | | |
|---|---|---|---|---|---|---|---|---|---|---|
| Components | F1 | F2 | F3 | F4 | F5 | F6 | F7 | F8 | F9 | F10 |
| Water | 100 | | | | | | | | | ad |
| Viscosity [mPas] | 30 | 30 | 26 | 30 | 40 | 40 | 40 | 40 | 40 | 40 |
| Crystal fineness | 1 | 1 | 1 | 1 | 2 | 3 | 3 | 3 | 3 | 4 |
| Pearlescence | 1 | 2 | 1 | 1 | 1 | 3 | 3 | 3 | 3 | 5 |
| Opacity | – | – | – | – | – | + | + | + | + | + |

*DEHYQUART ® F 75 (Henkel KGaA, Düsseldorf, FRG).

What is claimed is:

1. A hair treatment formulation comprising:
   a. 5–25% by weight of a sugar surfactant selected from the group consisting of cocoalkyloligoglucoside and lauric acid N-methyl glucamide;
   b. 2–5% by weight of a silicone compound selected from the group consisting of dimethyl polysiloxane and amodimethicone; and
   c. 0.5 to 1.5% by weight of a pearlescent wax selected from the group consisting of ethylene glycol distearate and lauric acid monoglyceride.

* * * * *